US009546564B2

United States Patent
Lewis (10) Patent No.: US 9,546,564 B2
(45) Date of Patent: Jan. 17, 2017

(54) ROTOR TIP CLEARANCE (71) Applicant: ROLLS-ROYCE PLC, London (GB)

(72) Inventor: Leo Vivian Lewis, Kenilworth (GB)

(73) Assignee: ROLLS-ROYCE plc, London (GB)

( * ) Notice: Subject to any disclaimer, the term of this patent is extended or adjusted under 35 U.S.C. 154(b) by 418 days.

(21) Appl. No.: 14/223,447

(22) Filed: Mar. 24, 2014

(65) Prior Publication Data

US 2014/0321985 A1 Oct. 30, 2014

(30) Foreign Application Priority Data

Apr. 29, 2013 (GB) .................................. 1307646.8

(51) Int. Cl.
- *F01D 11/20* (2006.01)
- *F01D 11/24* (2006.01)
- *G05B 15/02* (2006.01)
- *G01N 25/16* (2006.01)
- *F01D 11/18* (2006.01)

(52) U.S. Cl.
CPC ............... *F01D 11/24* (2013.01); *F01D 11/18* (2013.01); *F01D 11/20* (2013.01); *G01N 25/16* (2013.01); *G05B 15/02* (2013.01); *F05D 2260/81* (2013.01); *F05D 2270/44* (2013.01); *F05D 2270/71* (2013.01)

(58) Field of Classification Search
CPC ........... F01D 11/18; F01D 11/20; F01D 11/24; F05D 2260/81; F05D 2270/44; F05D 2270/71; G01N 25/16; G05B 15/02
See application file for complete search history.

(56) References Cited

U.S. PATENT DOCUMENTS 6,487,491 B1 * 11/2002 Karpman et al. ....... F01D 11/24 415/115

FOREIGN PATENT DOCUMENTS

| EP | 1 314 857 A2 | 5/2003 |
| WO | WO 2012/001726 A1 | 1/2010 |

OTHER PUBLICATIONS

British Search Report issued in British Patent Application No. GB1307646.8 on Oct. 25, 2013.

* cited by examiner

*Primary Examiner* — Audrey K Bradley
(74) *Attorney, Agent, or Firm* — Oliff PLC (57) ABSTRACT

A method of characterizing mechanical and thermal growth of a rotor tip clearance arrangement and a method of controlling such an arrangement. The characterization method comprising constructing a finite element model and calibration cases; run the model for the calibration cases to obtain displacements; and calculating component growth therefrom. The growth is characterized and scaled for the operating conditions. The clearance is calculated in a time step from the growths and input to a control arrangement for subsequent time steps.

20 Claims, 8 Drawing Sheets

ROTOR TIP CLEARANCE

The present invention relates to a method of characterising mechanical and thermal growth of rotor tip components and to a method of controlling the resultant clearance between the rotor tip and surrounding casing.

EP 1314857 discloses a method of characterising mechanical growth of rotor tip components on the basis of the masses of the components. It also discloses controlling clearance based on the mechanical growth.

One disadvantage of this method is that the component growth calculation is not well adapted for transient growth caused by thermal fluctuations. As a result, the rotor tip components controlled to this method may transiently rub, which subsequently increases all clearances between the components, or may transiently comprise large clearances, which decreases efficiency and therefore increases fuel usage.

The present invention provides a method of characterising component growth and a method of controlling rotor tip clearance that seeks to address the aforementioned problems. It finds particular utility for rotor stages of a gas turbine engine in which minimising tip clearance without causing tip rub results in significant fuel savings.

Accordingly the present invention provides a method of characterising mechanical and thermal growth of a rotor tip clearance arrangement, comprising steps to:
  construct a finite element model of components in the rotor tip clearance arrangement;
  define reference points on components in the model;
  define calibration cases for the model;
  run the model for each calibration case and record displaced position of each reference point;
  calculate component growth from the reference points and displaced positions;
  characterise the component growth as comprising mechanical growth and thermal growth;
  interpolate mechanical growth and thermal growth between calibration cases; and
  output a mechanical growth and thermal growth characterisation map.

Advantageously the method enables growth of the components forming a rotor and casing to be accurately calculated and characterised. The growths are then scaled for all engine operating conditions and recorded in a map that can be referenced for real-time control of the rotor tip clearance arrangement. The map may be graphical, tabular, one or more functions or equations, or any other suitable reference format.

The steps may be performed off-line. Advantageously the mechanical growth and thermal growth characterisation map can be produced once and retained for subsequent use of the rotor tip clearance arrangement.

The calibration cases may include a calibration case in which no thermal strain is present. Advantageously, such a calibration case results in mechanical growth but no thermal growth. The calibration cases may include a sea level calibration case and an altitude calibration case. Advantageously, such cases may bound the engine operating envelope for growth dependence on altitude. The calibration cases may include sea level and altitude calibration cases combined with controlled tip clearance displacement. Advantageously such cases include the effect of changing the clearance, mechanically or otherwise, on the growths. The thermal growth may comprise the component growth minus the mechanical growth for calibration cases that include thermal strain.

The mechanical growth and thermal growth may be extrapolated for engine operating conditions outside the calibration cases and interpolated between calibration cases. The mechanical growth may be interpolated using a pressure difference.

The thermal growth may comprise steady-state thermal growth and transient thermal growth. Advantageously the stead-state and transient thermal effects on growth can be separately calculated and mapped using the method of the present invention.

The transient thermal growth may be calculated using a time constant. The time constant may be a function of an engine parameter; an aircraft parameter two or more engine parameters; two or more aircraft parameters; or at least one engine parameter and at least one aircraft parameter. Advantageously, transient thermal growths calculated using such time constants are more accurate representations of the growth of the modelled components.

The transient thermal growth may be calculated using a heating time constant and a cooling time constant. The transient thermal growth may be calculated using a high power time constant and a low power time constant. Advantageously, using two or more different time constants enables the method to produce a more accurate representation of the transient thermal growths of the components modelled.

The method may comprise a further step to calculate an effective temperature of one of the components, or of each of the components. The effective temperature may be calculated from the steady-state thermal growth and the characteristic length of the component. The method may comprise a further step to calculate a non-dimensional stabilised temperature from the effective temperature. Advantageously the non-dimensional temperature can be used to extrapolate and interpolate the steady-state thermal growth for engine operating conditions outside the calibration cases.

The method may comprise a further step to measure displaced positions corresponding to the model reference points to validate the method. The measurements may be of the absolute displaced positions or of the relative position of the component features corresponding to the model reference points. The method validation need only be performed in testing so displacement probes need not be installed in engines when in service. Advantageously, the weight and consequent cost of displacement probes can be avoided.

The present invention also provides a method of controlling a rotor tip clearance arrangement at a time step comprising steps to:
  measure engine parameters;
  calculate the mechanical growth and thermal growth from the measured engine parameters and the map according to the method described above;
  calculate clearance between components from the calculated component growths; and
  control the rotor tip clearance arrangement to increase or decrease clearance based on the difference between the calculated clearance and a pre-defined clearance.

Advantageously, the method does not require displacement probes or other heavy components. Instead it uses engine parameters which are already measured on most engines. Beneficially, the method results in better clearance control.

The steps of the method may be performed during use of the rotor tip clearance arrangement. The steps may be iterated for each subsequent time step. The clearance may be calculated from the component growths calculated at the current and previous time steps. Advantageously, therefore, it is a real-time method.

The time step may be in the range 0.1 to 10 seconds. Preferably it may be in the range 100 to 200 milliseconds. Advantageously this is comparable to the measurement period of at least some engine parameters.

The method may further comprise a step before the step to measure engine parameters to initialise component growths and clearance. This may be achieved by measurement or calculation from the component growths and clearance at last engine shut down.

The present invention also provides a rotor tip clearance arrangement comprising a rotor blade having a tip; a rotor stage casing surrounding the rotor blade and defining a clearance with the tip; a clearance arrangement to increase or decrease the clearance; and a controller to control the clearance arrangement. The controller may comprise an engine electronic controller. The controller is adapted to carry out the methods described above. Advantageously, the rotor tip clearance arrangement is more accurate than known arrangements.

The present invention also provides a gas turbine engine comprising a rotor tip clearance arrangement as described.

The present invention provides a computer program having instructions adapted to carry out the methods described; a computer readable medium, having a computer program recorded thereon, wherein the computer program is adapted to make the computer execute the methods described; and a computer program comprising the computer readable medium as described.

Any combination of the optional features is encompassed within the scope of the invention except where mutually exclusive.

The present invention will be more fully described by way of example with reference to the accompanying drawings, in which.

Figure 1:
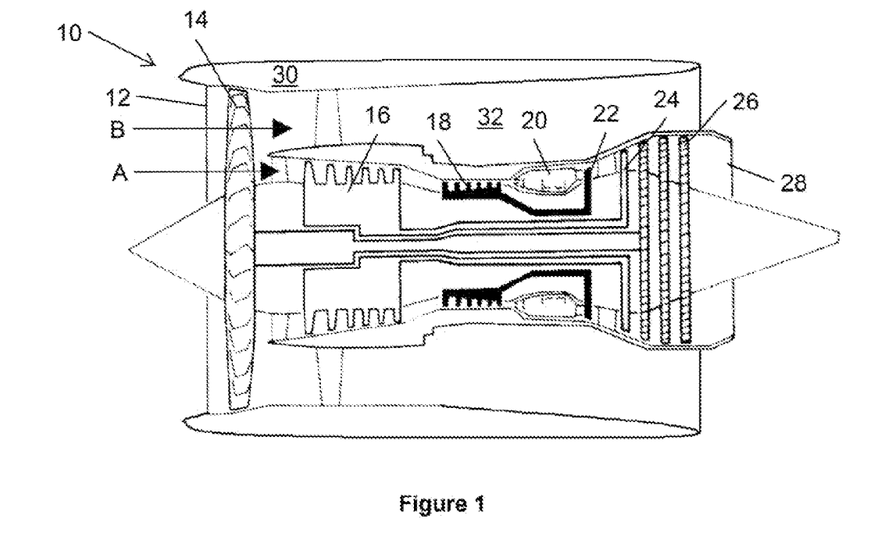
FIG. 1 is a sectional side view of a gas turbine engine.

A gas turbine engine 10 is shown in FIG. 1 and comprises an air intake 12 and a propulsive fan 14 that generates two airflows A and B. The gas turbine engine 10 comprises, in axial flow A, an intermediate pressure compressor 16, a high pressure compressor 18, a combustor 20, a high pressure turbine 22, an intermediate pressure turbine 24, a low pressure turbine 26 and an exhaust nozzle 28. A nacelle 30 surrounds the gas turbine engine 10 and defines, in axial flow B, a bypass duct 32.

Figure 2:
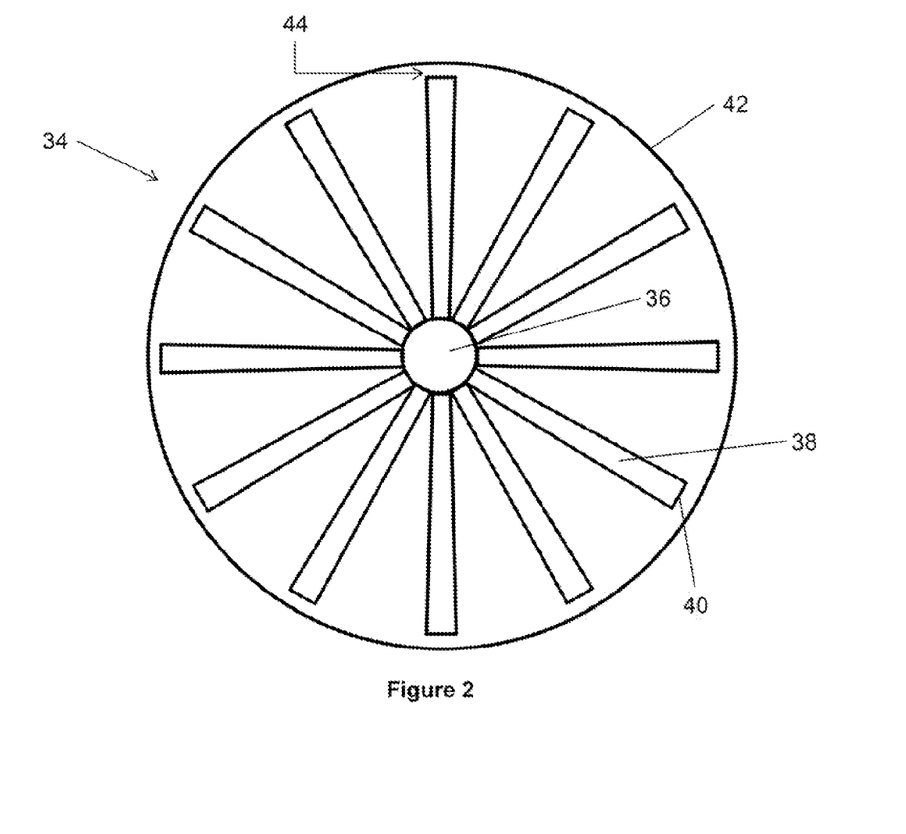
FIG. 2 is a schematic illustration of a rotor stage of a gas turbine engine.

Each of the fan 14, intermediate pressure compressor 16, high pressure compressor 18, high pressure turbine 22, intermediate pressure turbine 24 and low pressure turbine 26 comprises one or more rotor stages. A schematic illustration of a rotor stage 34 is shown in FIG. 2 comprising a rotor hub 36 from which radiate a plurality of blades 38. The blades 38 each comprise a blade tip 40 at the radially distal end from the hub 36. Radially outside the blade tips 40 is a rotor stage casing 42 which may include a segment assembly 56 comprising a plurality of segments forming its radially inner surface as will be understood by those skilled in the art. Between the blade tips 40 and the rotor stage casing 42 is a clearance 44.

In use of the gas turbine engine 10, working fluid (air) does work on the rotor blades 38 as it passes substantially axially through the engine 10. Working fluid that passes over the blade tips 40 through the clearance 44 does no useful work and therefore reduces the efficiency of the engine 10 and increases fuel consumption. However, the clearance 44 is necessary to prevent the blade tips 40 rubbing against the rotor stage casing 42 which causes damage to one or both components. Tip rub is a transient effect because the rub erodes the blade tip 40 or casing surface which results in the clearance 44 being increased and therefore the engine efficiency reducing.

Additionally the clearance 44 is not constant throughout use of the gas turbine engine 10. Taking the example of a gas turbine engine 10 used to power an aircraft, the rotor stage 34 components grow and shrink in response to centrifugal forces and temperature changes resulting from different engine operating conditions. Thus when the engine 10 is cold, before use, the rotor blades 38 have a defined radial length and the rotor stage casing 42 has a defined diameter and is annular. The components each grow or shrink by different amounts and with a different time constant governing the speed at which the growth or shrinkage occurs. The growth due to centrifugal forces is substantially instantaneous.

Figure 3:
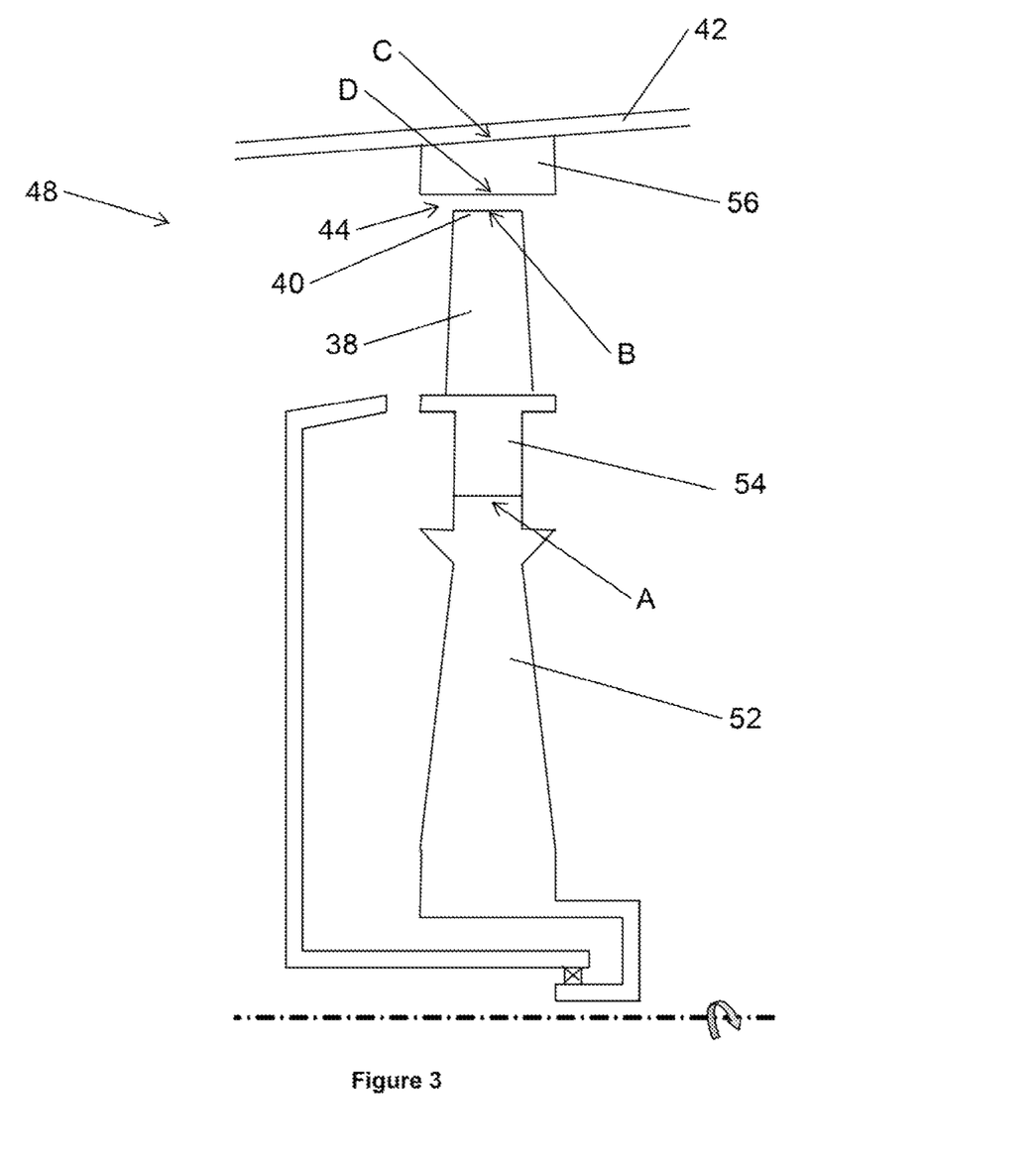
FIG. 3 is a schematic illustration of part of a modelled rotor stage for use in the method of the present invention.

FIG. 3 is an enlargement of part of the rotor stage as produced by a finite element model 48. The hub 36 is formed as a disc 52 upon which the plurality of rotor blades 38 is mounted. Each rotor blade 38 includes an integral blade root 54 which comprises suitable features, such as a fir tree shape, to enable secure mounting to the disc 52. Except where distinction is required the term rotor blade 38 in this description should be understood to include the blade root 54. The rotor stage rotor stage casing 42 optionally has a segment assembly 56 on its radially inner surface. The segment assembly 56 is comprised of a plurality of discontinuous segments in a circumferential array. The segments may be actively or passively controlled to move radially inwardly or outwardly to change the clearance 44 between them and the blade tips 40.

When the engine 10 is switched on it begins to heat up and the disc 52 and blades 38 begin to rotate which causes all the rotating components to grow radially. Due to the rotation of the rotor blades 38 and their relatively small mass the rotor blades 38 tend to grow radially very quickly, substantially instantly, by a small amount. The disc 52 grows radially outwardly by a relatively large amount, for example three times as much as the rotor blades 38, with a long time constant, for example 100 seconds. The rotor stage rotor stage casing 42 which is relatively massive and does not rotate grows by a relatively large amount, for example three times as much as the rotor blades 38, but with a long time constant, for example 50 seconds. The segment assembly 56 grows by a small amount, for example a third of the growth experienced by the rotor blades 38, with a moderate time constant, for example 15 seconds.

The segment assembly 56 grows radially inwardly whereas rotor stage rotor stage casing 42 and disc 52 grow radially outwardly and the rotor blades 38 elongate radially. Thus the clearance 44 reduces during engine acceleration phases of the flight such as ramp up and the start of take-off. Similarly, the clearance 44 increases during engine deceleration phases. There is a settling period after an engine acceleration or deceleration during which the clearance 44 may fluctuate before settling to a steady-state clearance 44.

It is known to apply active or passive tip clearance control arrangements to reduce the variation of clearance 44. For example cool air can be selectively delivered to passages in the rotor stage rotor stage casing 42 to cool the rotor stage casing 42 and thereby reduce the diameter or retard the growth of the diameter. Alternatively the segment assembly 56 radially inside the rotor stage rotor stage casing 42 can be moved mechanically to change the clearance 44.

The present invention relates to a more accurate method to characterise the radial growth of the rotor stage 34 components in terms of both mechanical and thermal growth. It also relates to the use of this characterised component growth to control tip clearance arrangements.

Figure 4:
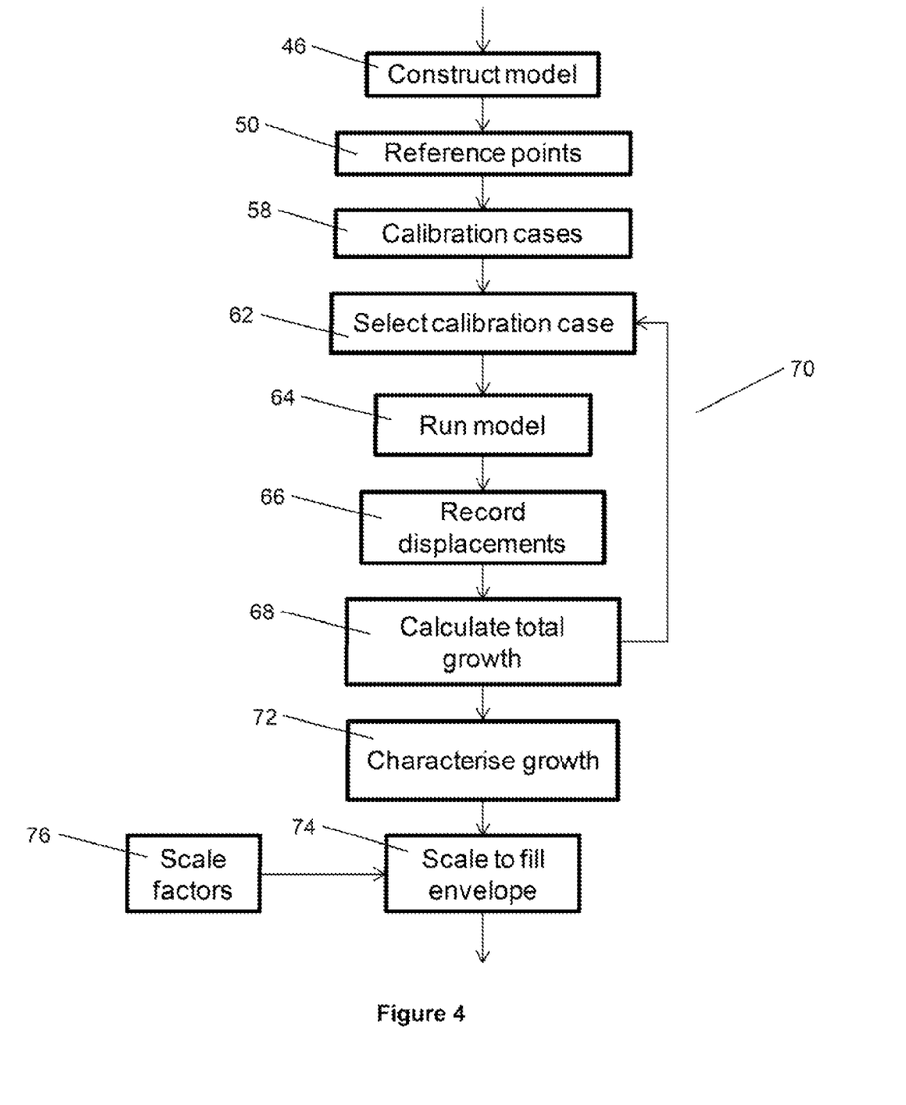
FIG. 4 is a flow chart of part of the method of the present invention.

A flow chart of the first part of the method is shown in FIG. 4. The first step of the method, shown in box 46, comprises constructing a finite element model 48 of components forming the rotor stage 34. The finite element model 48 therefore provides a mathematical (and graphical) representation of the disc 52, blade roots 54 and blades 38, rotor stage casing 42 and, indirectly, the clearance 44. A part of the model 48 is shown in FIG. 3. The finite element model 48 of the rotor stage 34 may be a subset of a larger finite element model, for example of the whole gas turbine engine 10 or a sub-system thereof such as the intermediate pressure turbine 24.

The second step of the method, shown in box 50, comprises defining reference points on the modelled components. The example in FIG. 3 defines four radially aligned reference points A, B, C, D as well as a null point at the rotational axis (not shown). The first reference point A is positioned where the disc 52 meets the blade root 54. The second reference point B is positioned at the blade tip 40. The third reference point C is positioned where the casing segment assembly 56 meets the rotor stage casing 42 and the fourth reference point D is positioned at the radially inner face of the segment assembly 56. The clearance 44 has radial extent between reference point B and reference point D. Beneficially the four reference points A, B, C, D mark the transitions between components that may be formed from different materials which each have different thermal capacity and therefore thermal growth rates.

For a rotor stage 34 having a segment assembly 56 radially inwardly of the rotor stage casing 42, four reference points A, B, C, D is the minimum requirement. If there is no segment assembly 56, reference point D can be omitted and the clearance 44 has radial extent between reference point B and reference point C. It is also possible to define more than four reference points. For example, in the rotor stage 34 illustrated in FIG. 3 it may be beneficial to define a fifth reference point at the radially inner surface of the disc 52. It may also be beneficial to have axial spacing between reference points. For example, the leading and trailing edges of the blade 38 may have different radial extent relative to the rotational axis. Defining a reference point at the blade tip 40 at each of the leading and trailing edges subsequently enables clearance 44 to be controlled at both these locations.

Figure 5:
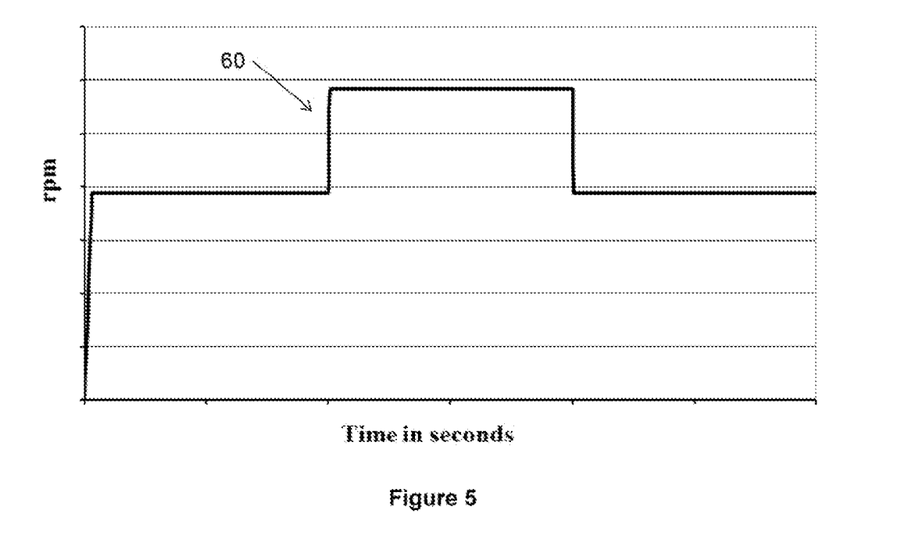
FIG. 5 is an exemplary plot of a calibration case.

The third step of the method, shown in box 58 of FIG. 4, comprises defining calibration cases 60 for use in running the model 48. The calibration cases 60 may take the form of a square wave rotational speed profile against time, an example of which is shown in FIG. 5. The calibration case 60 has a low power (speed) condition and a high power (speed) condition. It ramps very rapidly from low power to high power, holds at high power for a period and then ramps very rapidly back down to low power. The ramps are modelled as the fastest that are achievable in normal engine running and may each be of the order of 10-15 seconds. Preferably a calibration case 60 is also predicated with other constraints, such as the altitude at which the engine 10 is being operated, the mass flow of tip clearance control flow through the segment assembly 56, and the ambient temperature of the environment in which the engine 10 is operated. At least one calibration case 60 is defined for a high power condition, and therefore high rotational speed, with no thermal strains. This is achieved by using the temperatures only for determination of Young's Modulus for each component and excluding the calculation of thermal growths so only centrifugal and other mechanical growths are derived.

The fourth step of the method, shown in box 62 of FIG. 4, comprises selecting one of the calibration cases 60 from the set defined at the previous step 58. Each of the calibration cases 60 will be used within the method of the present invention.

The fifth step of the method, shown in box 64 of FIG. 4, comprises running the finite element model 48 using the selected calibration case 60. The output from the run comprises the displaced position $d_A$, $d_B$, $d_C$, $d_D$ of each reference point A, B, C, D from its initial position. In the sixth step of the method, box 66, these displaced positions $d_A$, $d_B$, $d_C$, $d_D$ are recorded.

The seventh step of the method, shown in box 68 of FIG. 4, comprises calculating total component growth for each calibration case 60. The component growth is calculated as the difference between the reference point positions A, B, C, D, and the displaced positions $d_A$, $d_B$, $d_C$, $d_D$. Optionally the subtraction can be arranged so that the calculated total growth is positive for growth of the component and negative for radial shrinkage of the component. Alternatively, the subtraction can be arranged so that the calculated total growth is positive in the radial direction away from the hub 36 and negative in the radial direction towards the hub 36. As will be apparent, the choice herein simply results in different signs in subsequent equations.

Figure 6:
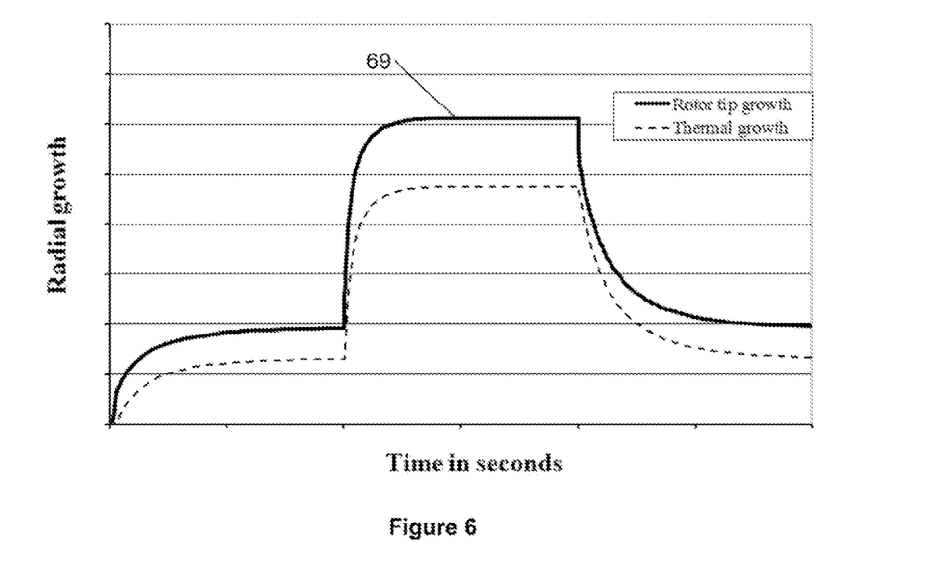
FIG. 6 is an exemplary plot of the radial growth of the blade tip.

FIG. 6 is an exemplary plot of the radial growth 69 of the blade tip 40, which is the difference between the displaced position $d_B$ and the original position of reference point B. It will be understood that equivalent plots can be produced for the radial growth of each of the components by plotting the difference between the original position of the reference points A, B, C, D and the displaced positions $d_A$, $d_B$, $d_C$, $d_D$.

The fourth 62, fifth 64, sixth 66 and seventh 68 steps of the method are iterated, as shown by loop 70, for each calibration case 60 in turn. The iteration loop 70 ends when the finite element model 48 has been run with each calibration case 60, the resultant displaced positions $d_A$, $d_B$, $d_C$, $d_D$ have been recorded and the component growth calculated therefrom.

The eighth step of the method, box 72 in FIG. 4, comprises characterising the component growth into mechanical growth and thermal growth. First the calibration case 60 with no thermal strain is used to calculate the mechanical growth. This datum value of mechanical growth is then scaled to fill the engine power condition envelope. For example, a scaling factor that is proportional to the shaft speed squared can be used, or a scaling factor that is dependent on any one or more of shaft speed squared, altitude, ambient temperature and/or pressure or any other engine or aircraft parameters.

The calibration cases 60 which include some thermal strain the component growth comprise the sum of mechanical growth and thermal growth. Thus thermal growth is the total component growth calculated at step 68 minus the mechanical growth scaled from the calibration case 60 with no thermal strain.

The thermal growth is further characterised as steady-state thermal growth or transient thermal growth. Steady-state thermal growth is the difference between the total component growth and the scaled mechanical growth for calibration cases 60 when at steady-state conditions. That is once the component growth response has stabilised to the elevated speed input portion of the square wave. An effective temperature $T_{EFF}$ can be calculated from the steady-state thermal growth divided by the product of the characteristic length of the component (that is the distance between the two reference points A, B, C, D that define its radial extent) and the thermal coefficient of expansion of the component material α (which may be temperature dependent). A non-dimensionalised temperature x can be calculated from the effective temperature $T_{EFF}$, a reference cold air temperature $T_{COLD}$ and a reference hot air temperature $T_{HOT}$. The reference cold air temperature $T_{COLD}$ and the reference hot air temperature $T_{HOT}$ are chosen from locations in the main gas path or bypass duct of the gas turbine engine 10. The non-dimensionalised temperature x is thus different for each component and may also vary between steady-state points in different calibration cases 60. The non-dimensional temperature x is a scale factor for the steady-state thermal growth.

Transient thermal growth is the difference between total component growth and scaled mechanical growth in periods which are not steady-state. Transient thermal growth is characterised by time constants which define the rate at which the component grows or shrinks due to transient thermal strains. Typically there are different time constants for heating from a low power to a high power condition and for cooling from a high power to a low power condition. The cooling time constant is generally longer than the heating time constant, for example 2 to 4 times longer. The time constants may also be dependent on altitude. Generally time constants are around twice as long at cruise altitude as at sea level.

Figure 7:
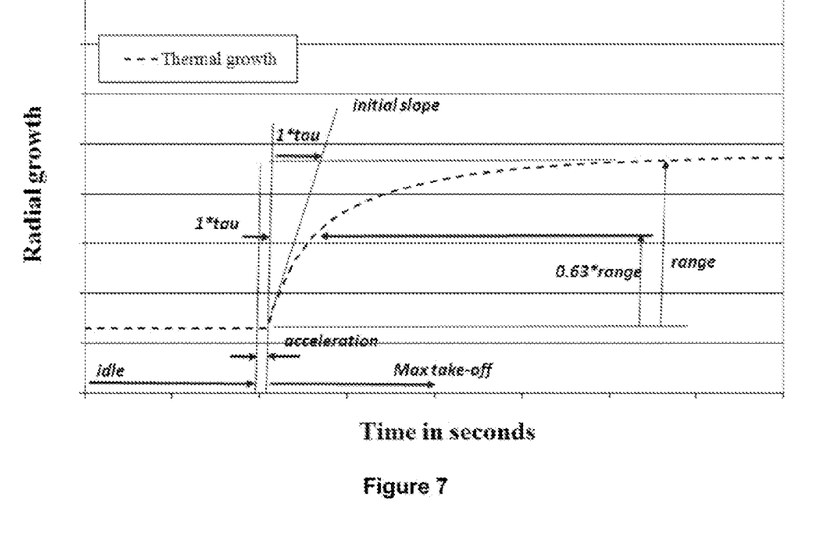
FIG. 7 is an exemplary plot of transient thermal growth.

A first approximation to the time constant for the transient thermal growth is the time taken to reach 63% of the stabilised, new steady-state thermal growth. This is because the radial growth is governed by $$(1 - e^{t/\tau}),$$

where t is the time interval and τ is the time constant. Alternatively, the time constant can be estimated from the initial gradient (first derivative) of the radial growth. The time constant can be refined, if required, by iterative methods to give the best overall fit to the heating or cooling growth curve. The two methods of first approximating the time constant τ are shown in FIG. 7.

In a ninth step of the method, shown in box 74 of FIG. 4, the mechanical growths, steady-state thermal growths and time constants for transient thermal growths characterised in the previous step 72 are scaled from datum values derived from the calibration cases 60. The scaling is applied to give component growth for conditions other than those considered in the calibration cases 60; that is any condition combinations in the engine operating envelope. Scale factors 76 are used in the scaling, which differ for the mechanical and thermal growths and the time constants.

Mechanical growths are scaled differently for the different components in the rotor stage 34. The disc 52 and blade 38 mechanical growths are scaled in proportion to rotational speed squared. The rotor stage casing 42 and segment assembly 56 mechanical growths are scaled in proportion to a gas path pressure difference. For example the pressure difference between compressor entry and compressor delivery, or between fan bypass and compressor delivery. Thus for mechanical growth the scale factors 76 are rotational speed squared and gas path pressure difference. These factors may be summed, particularly for long flexible rotor blades 38, or multiplied together to form the scale factor 76 as required. The casing axial tension may also be an input to the scale factor 76 for the mechanical growth.

Transient thermal growths are scaled by scaling the steady-state non-dimensionalised temperature x and the time constants. The scale factor 76 may be altitude, Mach number, ambient temperature, engine thrust or rotational speed. Alternatively the scale factor 76 may be a combination of two or more of these factors.

Figure 8:
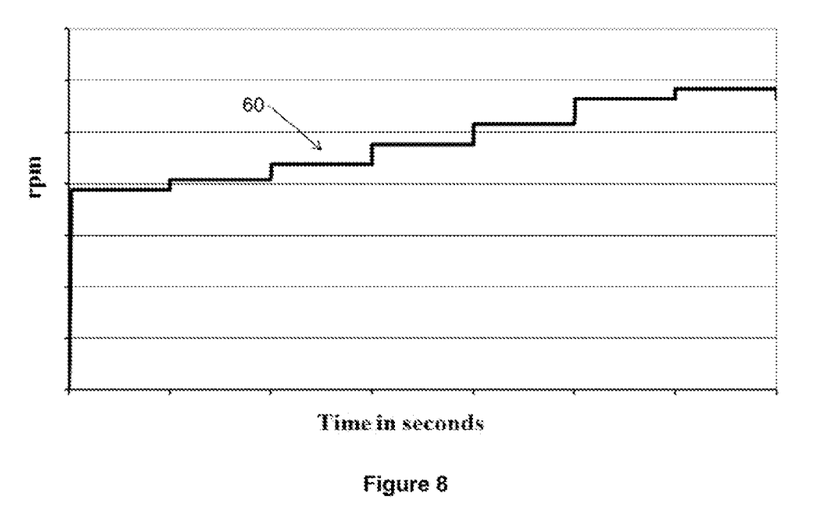
FIG. 8 is an exemplary plot of another calibration case.

The amount of scaling required at step 74 can be reduced by using more calibration cases 60 at the expense of processing capacity to run the finite element model 48 for all the calibration cases 60. For example, the altitude-dependence of a scale factor 76 can be improved by defining calibration cases 60 at more altitude settings. The non-dimensionalised temperature x can be improved by defining one or more calibration cases 60 that comprise incremental speed settings as shown in FIG. 8.

From the steps shown in FIG. 4 the method can output a map of the mechanical growth, non-dimensionalised temperature x for steady state thermal growth and time constants for transient thermal growth against inputs. For example, the growths can be mapped against engine power or speed. It may also be mapped against altitude and/or ambient conditions. The map may be a 2D or 3D graph or one or more look-up tables from which the output can be read, or the map may be one or more algorithms from which the output growths can be calculated. Preferably the map, howsoever constituted, takes account of whether the component is growing or shrinking, so that differing heating and cooling rates are encompassed. Graphically this may have the form of a hysteresis loop. Some conditions may be considered to have only one of a heating and a cooling rate. For example, take-off engine condition is only approached from slower speeds so only a heating rate is required. Similarly, idle is only approached from higher speeds so only a cooling rate is required. Other engine conditions can be approached from higher or lower speeds and therefore have a heating and a cooling rate.

The method described with respect to FIG. 4 can be performed off-line in engine development or pass-off phases and be loaded into computer memory. Preferably the output map is loaded into memory on board the engine 10, such as a dedicated memory or that associated with the engine electronic controller (EEC). It is then available for use in a method of controlling a rotor tip clearance arrangement 78 shown in FIG. 9.

Figure 10:
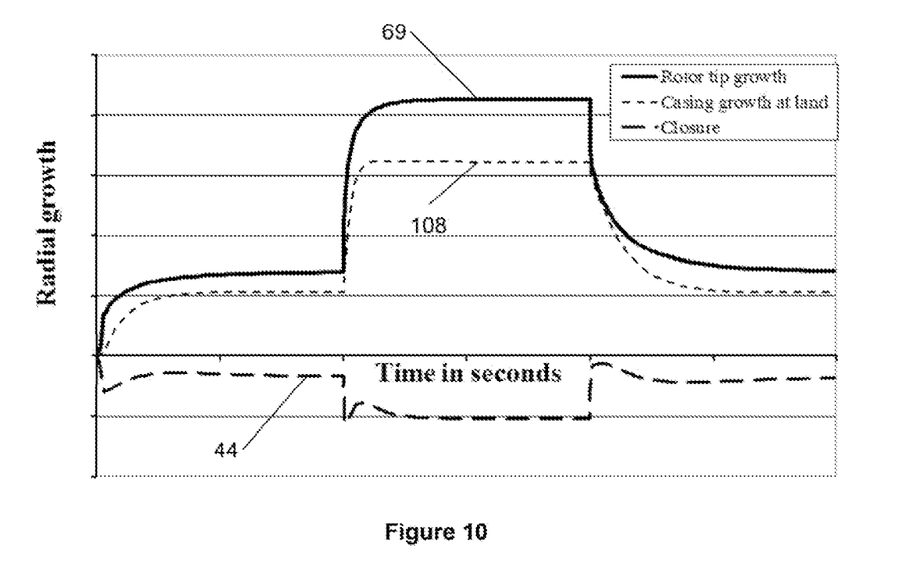
FIG. 10 is an exemplary plot of the radial growth of the blade tip and segment assembly, and the clearance.

FIG. 10 is an exemplary plot of the radial growth 69 of the blade tip 40, as shown in FIG. 6, for the calibration case 60 shown in FIG. 5. It also shows the radial growth 108 of the rotor stage casing 42, which is the difference between the displaced position $d_C$ and the original position of reference point C. FIG. 10 also shows the clearance 44 calculated from the net radial growth and initial component radial lengths. As can be seen, the clearance 44 has a complex shape through the calibration cycle 60 due to the different transient thermal growth time constants τ applicable for the components and the different total radial growths of each component.

Figure 9:
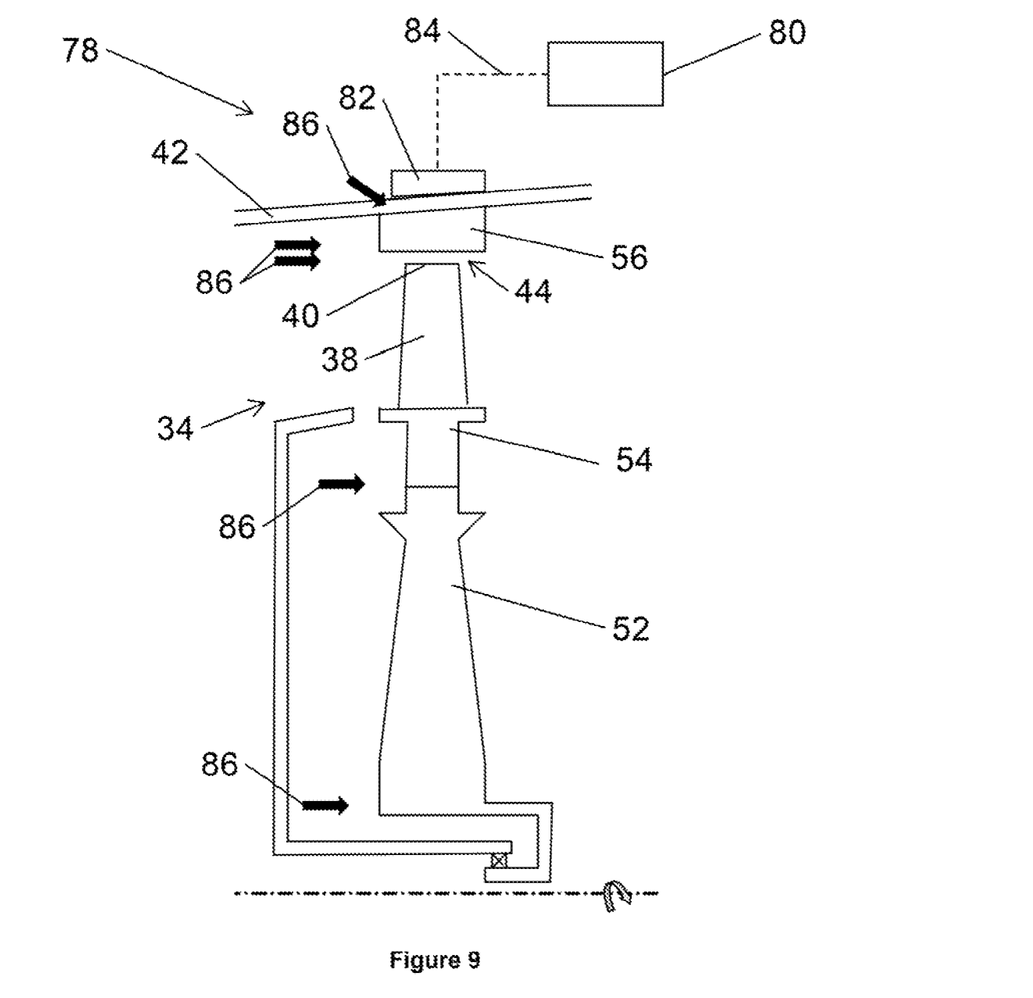
FIG. 9 is a schematic illustration of part of a rotor tip clearance arrangement according to the present invention.

The rotor tip clearance arrangement 78 comprises the rotor stage 34 and rotor stage casing 42 (with or without a segment assembly 56). It also comprises a controller 80 incorporating a processor and memory, and a clearance arrangement 82 that can be controlled via signal line 84 to change the clearance 44 between the blade tip 40 and the radially inner surface of the segment assembly 56 or rotor stage casing 42. The controller 80 may form part of or be a function of the engine electronic controller, may be a dedicated controller 80 or may form part of or be a function of another controller within the engine 10. The clearance arrangement 82 can take any suitable form. For example, it may be an arrangement of pipes and valves to selectively deliver cool air to the rotor stage casing 42 or segment assembly 56 to change the growth rates and thereby adjust the clearance 44. Alternatively it may be a mechanical arrangement to move the segment assembly 56 or portions of the rotor stage casing 42 radially to change the clearance 44.

For validation of modelled component growths, for example during development phases of an engine, the rotor tip clearance arrangement 78 may also include displacement probes 86 positioned and arranged to measure the position of points on the components that correspond to the model reference points A, B, C, D. There may be a displacement probe 86 for each radial location of points or a displacement probe 86 may be arranged to measure the position of more than one point. Alternatively the displacement probes 86 may be arranged to measure the distance between two points that are equivalent to the model reference points A, B, C, D rather than their absolute positions.

The measured displaced positions may be supplied to the controller 80 via signal line 84. Within the processor comprised in the controller 80, the current clearance 44 is calculated using the measured displaced positions with reference to the mapped component mechanical growth and thermal growth. The controller 80 then compares the current clearance 44 with a pre-defined optimal or desired clearance 44, if the current and pre-defined clearances 44 differ by more than a pre-defined margin, the controller 80 generates a control signal which is passed along signal line 84 to the clearance arrangement 82. The control signal causes the clearance arrangement 82 to move the segment assembly 56 or rotor stage casing 42 to increase or decrease the clearance 44 as appropriate.

Figure 11:
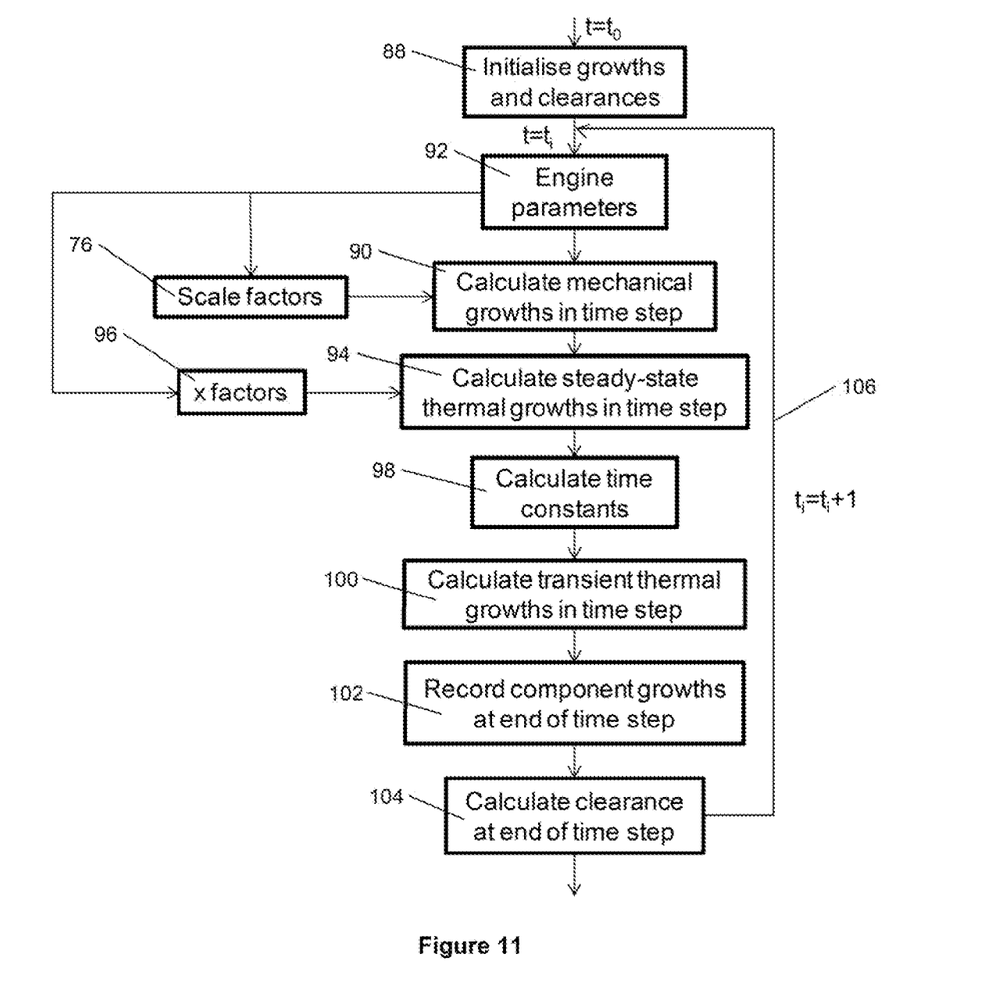
FIG. 11 is a flow chart of part of the method of the present invention.

The present invention also provides a method of controlling the rotor tip clearance arrangement 78 which in shown in the flow chart in FIG. 11. The method is applied in real-time during use of the engine 10 to actively control the tip clearance 44 to optimise the clearance 44 for improved fuel efficiency of the engine 10. The method is iterated in time steps t, for example in the range of 0.1 to 10 seconds, preferably approximately 1 second.

In a first step 88, the growths and clearances are initialised. The initial scaled mechanical growths are determined on the basis of the engine parameters at initialisation. An effective temperature $T_{EFF}$ for each component is assigned. This may be measured directly or calculated on the basis of ambient conditions at initialisation. The initial thermal growths, which are assumed to be steady-state with no transient component, can then be calculated. The initial clearance can be calculated from the initial mechanical and steady-state thermal growths.

In a second step, the engine parameters 92 at a first time step t are obtained.

In a third step 90 the mechanical growth of each component is calculated for the first time step $t_1$. The mechanical growth is scaled from the calibration cases 60 as described above. The scale factor 76 for each component is determined from the engine parameters 92 at that time step, either by looking up a table or graph of the previously calculated scale factors 76 or by real-time calculation.

In a fourth step 94, the steady-state thermal growth in the first time step $t_1$ is derived for each component. The engine parameters 92 at that time step are input to the fourth step 94 for the calculation. The steady-state thermal growth in the first time step $t_1$ and the effective temperature $T_{EFF}$ are calculated as described above.

In a fifth step 98, the time constant τ for each component for the transient thermal growth in the first time step $t_1$ is determined. In a preferred embodiment, the time constant τ for each component is looked up, in a reference table or the like, or calculated as a function of the engine parameters 92 or aircraft parameters such as altitude or shaft speed.

In the sixth step 100 of the method the time constants τ calculated at the fifth step 98 are used to calculate the transient thermal growth for each component in the first time step $t_1$.

The total growth of each component at the end of the first time step $t_1$ is calculated from the sum of the mechanical growth, steady-state thermal growth and transient thermal growth in the first time step $t_1$ and subtracted from the initial growth. These component growths are recorded in the seventh step 102 of the method.

In the final step 104 of the method the clearance 44 at the end of the first time step $t_1$ is calculated from the component growths determined in the previous step 102. Thus the clearance 44 is the net growth of the components subtracted from the initial clearance.

An iteration loop 106 increments the time step $t_i$ such that the component growths and clearance at the end of the first time step $t_1$ are used in the next time step $t_2$ in place of the initial growths and clearance. Thus the second pass through the method shown in FIG. 11 outputs the component growths and clearance at the end of the second time step $t_2$ which are passed to the second step 90 of the method for the subsequent iteration. The method is iterated for each time step $t_n$ where n is governed by the engine operating period or desired clearance control period.

Preferably the clearance 44 calculated in the final step 104 of the method can be passed to a control arrangement. The calculated clearance 44 can be compared to a desired clearance 44 for the engine operating condition. If the calculated clearance 44 is greater than the desired clearance 44 by a predetermined margin the control arrangement may cause the segment assembly 56 or rotor stage casing 42 to move radially inwards to close the clearance 44 or may cause a flow of cooling air to be passed through the segment assembly 56 or rotor stage casing 42 to change the thermal growth and thereby decrease the clearance 44. If the calculated clearance 44 is smaller than the desired clearance 44 by a predetermined margin, increasing the risk of tip rub, the control arrangement may cause the segment assembly 56 or rotor stage casing 42 to move radially outwards to increase the clearance 44. The predetermined margins may be the same or different for the size of the calculated clearance 44 relative to the desired clearance 44.

The steps for controlling the rotor tip clearance arrangement 78 are thus iterated to enable the clearance 44 to be actively managed. The time steps $t_n$ may be in the range of 0.1 to 10 seconds. For preferred embodiments of the present invention the time steps $t_n$ is at the low end of that range, for example 100 to 200 milliseconds. This is similar to the measurement frequency of control parameters in a gas turbine engine 10 and is therefore within the processing capacity of suitable controllers 80. As will be appreciated, the calculations can only be updated by new engine parameters 92 for calculation of the scale factors 76 and x factors 96. However, it is appropriate to match the measurement and calculation periods to the frequency at which the clearance arrangement 82 can act to change the clearance 44.

The method of the present invention is preferably encompassed in computer-implemented code and stored on a computer-readable medium. It is thus a computer-implemented method of characterising mechanical and thermal growth of a rotor tip clearance arrangement 78 and of controlling such an arrangement. The method may be implemented on a basic computer system comprising a processing unit and memory. There may be a user interface such as a keyboard and/or mouse, and display means to allow interrogation of the system during maintenance activity. During active control of the rotor tip clearance arrangement 78 such interfaces are unlikely to be required. The memory may comprise both temporary memory, to store measurements and calculations during application of the method, and long-term storage memory, to record some or all of the measurements, calculations and control signals for later review. The stored data may be transmitted during or after the engine flight cycle or downloaded after the engine flight cycle.

Although a finite element model 48 has been described, any suitable model may be used. Square wave calibration cases 60 have been described as these are common test cycle engine operating profiles. However, more complex calibration cases 60 can be used which more closely mirror expected operating profiles of the engine 10.

Although linear scale factors 76 or combinations of scale factors 76 have been described, the scale factors 76 may be applied in a non-linear function. Thus the scaling may be more aggressive in portions of the operating envelope than in other portions of it. For example, the scaling may be more aggressive for extrapolated portions than for interpolated portions, or may be more aggressive for portions of the envelope that are furthest from any calibration cases 60. There may be a polynomial, parabolic or exponential dependence on one or more scale factor 76 for some or all of the operating envelope.

Alternatively the scale factor 76 for the transient thermal growth may have inverse dependence on a convective heat transfer function as convection is the dominant heat transfer mechanism affecting the time constants.

The iteration period has been envisaged as constant so that the displaced positions of the points on the components are measured at a fixed time interval, for example between 0.1 and 10 second intervals, preferably around 1 second intervals or slightly more frequent. However, the time interval could be variable instead. For example, a short time interval could be used when the component is growing or shrinking quickly, during take-off or other transient engine events, and then a longer time interval used when the component is not changing so quickly, during cruise or other steady-state engine conditions. This reduces the calculation and recording burden overall for the engine cycle without compromising rapid control of the clearance 44 when necessary. The methods make no other distinction between steady-state and transient periods in the engine cycle.

There may be a fast time constant and a slow time constant defined for transient thermal growth. The growth is then calculated using a weighted sum of those calculated from the fast and slow time constants.

Although the method is used to control the clearance 44, the calculated clearance 44 can also be supplied to other control arrangements in the engine 10. For example the clearance 44 can be used to schedule bleed valves in the compressors to manage surge margin availability.

The invention claimed is:

1. A method of characterizing mechanical and thermal growth of a rotor tip clearance arrangement, comprising:
   constructing a finite element model of components in the rotor tip clearance arrangement;
   defining reference points on components in the model;
   defining calibration cases for the model;
   running the model for each defined calibration case and recording displaced position of each defined reference point;
   calculating component growth from the defined reference points and recorded displaced positions;
   characterising the component growth as comprising mechanical growth and thermal growth;
   interpolating mechanical growth and thermal growth between calibration cases; and
   outputting a mechanical growth and thermal growth characterisation map that is used to set rotor tip clearance of the rotor tip clearance arrangement.

2. The method as claimed in claim 1 wherein the method is performed off-line.

3. The method as claimed in claim 1 wherein the calibration cases include a calibration case in which no thermal strain is present and wherein mechanical growth is calculated from the calibration case having no thermal strain.

4. The method as claimed in claim 1 wherein the mechanical growth is interpolated using a pressure difference.

5. The method as claimed in claim 1 further comprising steps to measure displaced positions corresponding to the model reference points to validate the model.

6. The method as claimed in claim 1 wherein the calibration cases include a sea level calibration case, an altitude calibration case, and sea level and altitude calibration cases combined with controlled tip clearance displacement.

7. The method as claimed in claim 6 wherein the thermal growth comprises component growth minus mechanical growth.

8. The method as claimed in claim 1 further comprising calculating an effective temperature of one of the components.

9. The method as claimed in claim 8 further comprising calculating a non-dimensional stabilised temperature from the effective temperature.

10. The method as claimed in claim 1 wherein the thermal growth comprises steady-state thermal growth and transient thermal growth and wherein the transient thermal growth is calculated using a time constant.

11. The method as claimed in claim 10 wherein the time constant is a function of an engine parameter.

12. The method as claimed in claim 10 wherein:
    the transient thermal growth is calculated using a heating time constant and a cooling time constant; or
    the transient thermal growth is calculated using a high power time constant and a low power time constant.

13. A method of controlling a rotor tip clearance arrangement at a time step comprising:
- measuring engine parameters;
- calculating mechanical growth and thermal growth from measured engine parameters and a map according to the method of claim 1;
- calculating clearance between components from the calculated component growths; and
- controlling the rotor tip clearance arrangement to increase or decrease clearance based on the difference between the calculated clearance and a pre-defined clearance.

14. The method as claimed in claim 13 wherein the method is performed during use of the rotor tip clearance arrangement.

15. The method as claimed in claim 13 wherein:
- the method is iterated for each subsequent time step; and
- the clearance between the components is calculated from the component growths calculated at a current and previous time step.

16. The method as claimed in claim 13 further comprising initialising the component growths and the clearance prior to measuring the engine parameters.

17. A non-transitory computer-readable medium having a computer program recorded thereon, the program comprising instructions for:
- constructing a finite element model of components in a rotor tip clearance arrangement;
- defining reference points on components in the model;
- defining calibration cases for the model;
- running the model for each defined calibration case and recording displaced position of each defined reference point;
- calculating component growth from the defined reference points and recorded displaced positions;
- characterising the component growth as comprising mechanical growth and thermal growth;
- interpolating mechanical growth and thermal growth between calibration cases; and
- outputting a mechanical growth and thermal growth characterisation map that is used to set rotor tip clearance of the rotor tip clearance arrangement.

18. A method of controlling a rotor tip clearance arrangement at a time step, the method comprising:
- generating a mechanical growth and thermal growth characterisation map by:
  - constructing a finite element model of components in the rotor tip clearance arrangement;
  - defining reference points on components in the model;
  - defining calibration cases for the model;
  - running the model for each defined calibration case and recording displaced position of each defined reference point;
  - calculating component growth from the defined reference points and recorded displaced positions;
  - characterising the component growth as comprising the mechanical growth and the thermal growth;
  - interpolating the mechanical growth and the thermal growth between calibration cases; and
  - generating the mechanical growth and thermal growth characterisation map based on the interpolation;
- receiving measured engine parameters, the parameters having been measured by at least one engine sensor;
- calculating mechanical growth and thermal growth from the measured engine parameters and the mechanical growth and thermal growth characterisation map;
- calculating clearance between components based on the generated map; and
- outputting an instruction to control the rotor tip clearance arrangement to increase or decrease clearance based on the difference between the calculated clearance and a pre-defined clearance.

19. A rotor tip clearance arrangement comprising:
- a rotor blade having a tip;
- a rotor stage casing surrounding the rotor blade and defining a clearance with the tip;
- a clearance adjustment arrangement to increase or decrease the clearance; and
- a processor programmed to:
  - construct a finite element model of components in the rotor tip clearance arrangement;
  - define reference points on components in the model;
  - define calibration cases for the model;
  - run the model for each defined calibration case and record displaced position of each defined reference point;
  - calculate component growth from the defined reference points and recorded displaced positions;
  - characterise the component growth as comprising mechanical growth and thermal growth;
  - interpolate mechanical growth and thermal growth between calibration cases; and
  - output a mechanical growth and thermal growth characterisation map for setting rotor tip clearance of the rotor tip clearance arrangement.

20. A gas turbine engine comprising a rotor tip clearance arrangement as claimed in claim 19.

* * * * *